United States Patent
Holst et al.

(10) Patent No.: US 11,419,662 B2
(45) Date of Patent: Aug. 23, 2022

(54) APPARATUS FOR TISSUE ABLATION USING RADIOFREQUENCY ENERGY AND METHOD OF USE

(71) Applicant: Vive Scientific LLC, Southlake, TX (US)

(72) Inventors: Peter Axel Holst, Los Altos, CA (US); Michael John Hammond, Monona, WI (US); James Angus Boonzaier, Cambridge (GB)

(73) Assignee: VIVE SCIENTIFIC LLC, Southlake, TX (US)

( * ) Notice: Subject to any disclaimer, the term of this patent is extended or adjusted under 35 U.S.C. 154(b) by 464 days.

(21) Appl. No.: 16/363,892

(22) Filed: Mar. 25, 2019

(65) Prior Publication Data

US 2020/0305953 A1 Oct. 1, 2020

(51) Int. Cl.
| | |
|---|---|
| *A61B 18/14* | (2006.01) |
| *A61B 18/12* | (2006.01) |
| *A61B 5/00* | (2006.01) |
| *A61B 18/00* | (2006.01) |

(52) U.S. Cl.
CPC .......... *A61B 18/14* (2013.01); *A61B 18/1206* (2013.01); *A61B 5/0084* (2013.01); *A61B 2018/00577* (2013.01)

(58) Field of Classification Search
CPC ... A61B 18/14; A61B 18/1206; A61B 5/0084; A61B 2018/00577; A61B 5/1076; A61B 5/0088; A61B 5/6847; A61B 13/00; A61B 2090/309; A61B 90/30; A61B 2090/065; A61B 2017/00057; A61B 18/1485; A61B 2018/1475; A61B 2018/143; A61B 90/36
See application file for complete search history.

(56) References Cited

U.S. PATENT DOCUMENTS

| | | | |
|---|---|---|---|
| 4,811,733 A * | 3/1989 | Borsanyi | A61B 18/1485 606/45 |
| 6,045,549 A * | 4/2000 | Smethers | A61B 18/1477 606/39 |
| 6,390,978 B1 * | 5/2002 | Irion | A61B 5/0066 600/437 |
| 2006/0265031 A1 * | 11/2006 | Skwarek | A61M 3/0258 607/88 |
| 2008/0255461 A1 * | 10/2008 | Weersink | A61B 18/24 600/476 |
| 2012/0316398 A1 * | 12/2012 | Ashcraft | A61B 1/00048 600/188 |
| 2014/0058244 A1 * | 2/2014 | Krocak | A61B 18/12 600/407 |
| 2014/0180034 A1 * | 6/2014 | Hoseit | A61B 5/0066 600/301 |

(Continued)

*Primary Examiner* — Linda C Dvorak
*Assistant Examiner* — Lindsay Regan Lancaster
(74) *Attorney, Agent, or Firm* — Polsinelli PC; Adam C. Rehm; Zachary D. Cleary

(57) ABSTRACT

An apparatus for tissue ablation using radiofrequency energy comprises a housing extending from a first end to a second end. One or more pipes extend from the first end and each of the one or more pipes terminates at a tip. Each tip includes a light source operable to provide light. The apparatus further comprises a probe extending from some of the one or more pipes. Each probe is operable to deliver RF energy and to extend from or retract into the tip.

20 Claims, 5 Drawing Sheets

(56) References Cited

U.S. PATENT DOCUMENTS

2016/0066977 A1\* 3/2016 Neal, II ................. A61B 18/18
 606/34
2016/0066979 A1\* 3/2016 Mueller ............... A61B 5/0084
 600/477

\* cited by examiner

APPARATUS FOR TISSUE ABLATION USING RADIOFREQUENCY ENERGY AND METHOD OF USE

BACKGROUND

1. Field

The following description relates to tissue ablation and, more specifically, to an apparatus for tissue ablation using radio-frequency energy.

2. Description of Related Art

Sleep apnea affects many people and may cause sleep deprivation, snoring, insomnia, and various other symptoms obstructive to a person's health and wellbeing. Sleep apnea may be treated by several applications of tissue ablation using radiofrequency energy spread over several weeks. Conventional devices for tissue ablation suffer from various deficiencies. Among others, conventional devices may not be able to distinguish between treated tissue, untreated tissue, and various transitional states of tissue. As such, a practitioner applying a treatment may rely on experience and spacing treatments at predefined distances, which may be inaccurate or incorrectly spaced. Conventional devices may also not provide illumination at a site of treatment. As such, a practitioner may rely on an external source of light, such as a headlamp. Further, conventional devices may not communicate a progress or completion of a treatment. As such, a practitioner may rely on communication from another person monitoring the progress or completion or treatment on a progress screen away from the practitioner's line of sight.

Accordingly, there exists a need for an apparatus for tissue ablation using radiofrequency energy that does not suffer from the aforementioned deficiencies, and that is operable to distinguish between firmness of tissue, provide illumination at a site of treatment, and directly communicate progress of treatment to the practitioner.

SUMMARY

The present inventive concept provides an apparatus for delivering radio-frequency (RF) energy. The apparatus may include a housing extending from a first end to a second end. The apparatus may include a handle positioned at the second end of the housing. The housing may further comprise a progress indicator operable to indicate a progress or a completion of an event. The event may be a portion of a light path received.

The apparatus may include one or more pipes extending from the first end of the housing. Each of the one or more pipes may terminate at a tip. Each tip may have a light source operable to provide light. The apparatus may include a tongue depressor extending from the first end of the housing and coupled to the tip of each of the one or more pipes. The tongue depressor may include a center rib.

The apparatus may include a probe extending from some of the one or more pipes. Each probe may be operable to deliver RF energy. Each probe may be operable to extend from or retract into the tip. The event indicated by the progress indicator may be delivery of RF energy from a probe extending from one or more pipes.

The apparatus may include a light source protruding from the tip of each of the one or more pipes. The light source may be operable to send or more light paths. Each of the one or more pipes may include a hollow core to receive a wire for each light source. Each wire may connect each light source to a power source.

The apparatus may include a sensor operable to receive a portion of the light path. The sensor may be housed in light housing. The light housing may positioned at the tip of each of the one or more pipes. The portion of the light path received may indicate a thickness of a tissue. The apparatus may include another sensor operable to detect a force received from a user of the apparatus.

The aforementioned may be achieved in an aspect of the present inventive concept by providing a method of determining a thickness of a tissue. The method may include the step of transmitting, by one or more light sources, one or more light paths into a tissue of a patient. Each of the one or more light sources may extend from a tip of one or more pipes. Each of the one or more pipes may extend from a housing. The method may include the step of receiving, by one or more sensors, a portion of the one or more light paths. The one or more sensors may be housed in the tip of the one or more pipes. The method may include the step of notifying, by a progress indicator, a user of the thickness of the tissue. The notification may be based on the portion of the one or more light paths received. The method may include the step of delivering, via a probe, radio-frequency energy to the tissue. The probe may extend from some of the one or more pipes.

BRIEF DESCRIPTION OF THE DRAWINGS

The foregoing summary, as well as the following detailed description, will be better understood when read in conjunction with the appended drawings. For the purpose of illustration, there is shown in the drawings certain embodiments of the present disclosure. It should be understood, however, that the present inventive concept is not limited to the precise embodiments and features shown. The accompanying drawings, which are incorporated in and constitute a part of this specification, illustrate an embodiment of apparatuses consistent with the present inventive concept and, together with the description, serve to explain advantages and principles consistent with the present inventive concept.

DETAILED DESCRIPTION

Figure 1:
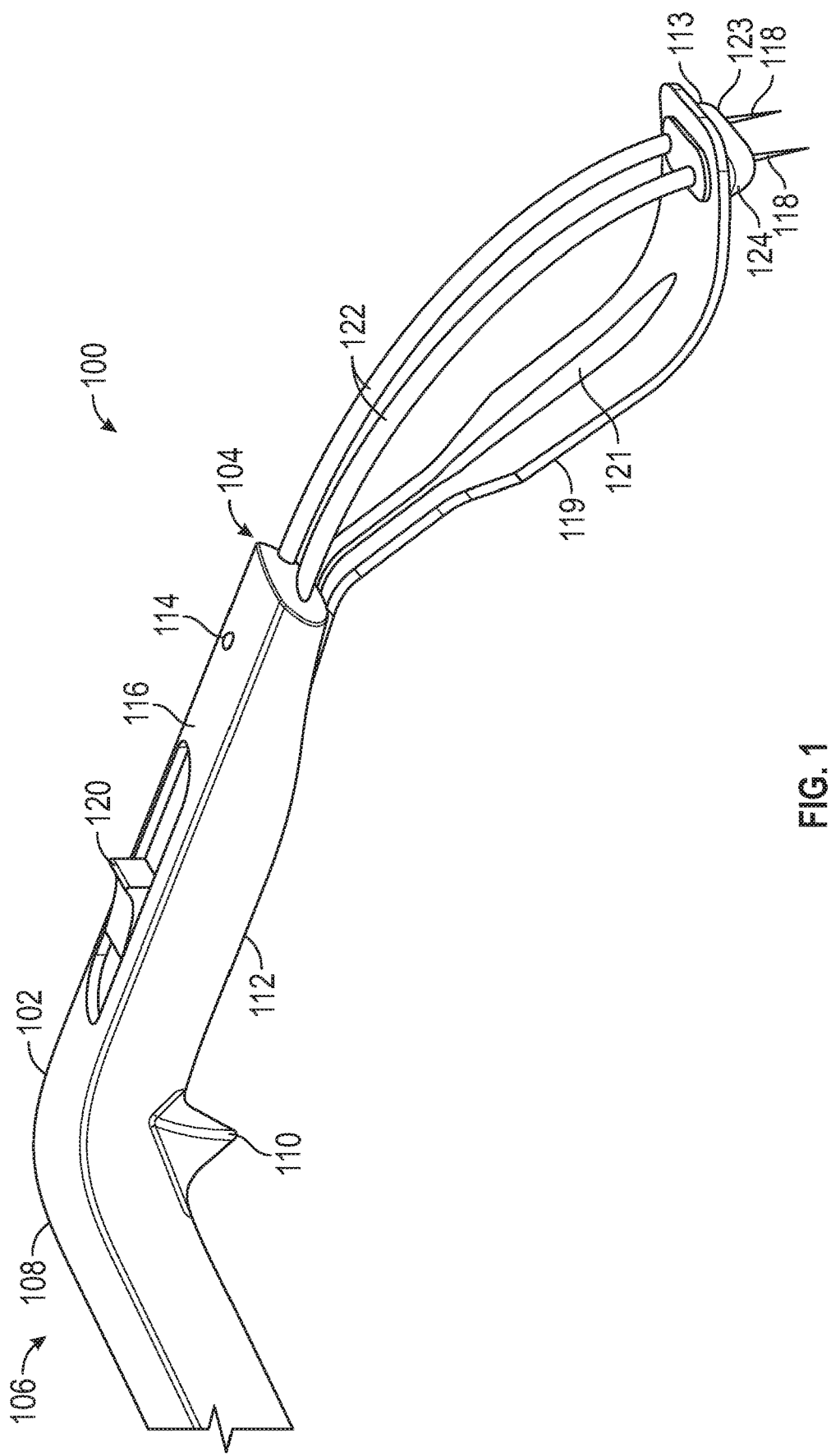
FIG. 1 is a diagram illustrating an isometric view of an apparatus for tissue ablation using radiofrequency (RF) energy.

It is to be understood that the present inventive concept is not limited in its application to the details of construction and to the embodiments of the components set forth in the following description or illustrated in the drawings. The figures and written description are provided to teach any person skilled in the art to make and use the inventions for which patent protection is sought. The present inventive concept is capable of other embodiments and of being practiced and carried out in various ways. Persons of skill in the art will appreciate that the development of an actual commercial embodiment incorporating aspects of the present inventive concept will require numerous implementations—specific decisions to achieve the developer's ultimate goal for the commercial embodiment. While these efforts may be complex and time-consuming, these efforts, nevertheless, would be a routine undertaking for those of skill in the art of having the benefit of this disclosure.

I. Terminology

The phraseology and terminology employed herein are for the purpose of description and should not be regarded as limiting. For example, the use of a singular term, such as, "a" is not intended as limiting of the number of items. Also, the use of relational terms such as, but not limited to, "top," "bottom," "left," "right," "upper," "lower," "down," "up," and "side," are used in the description for clarity in specific reference to the figures and are not intended to limit the scope of the present inventive concept or the appended claims. Further, it should be understood that any one of the features of the present inventive concept may be used separately or in combination with other features. Other systems, methods, features, and advantages of the present inventive concept will be, or become, apparent to one with skill in the art upon examination of the figures and the detailed description. It is intended that all such additional systems, methods, features, and advantages be included within this description, be within the scope of the present inventive concept, and be protected by the accompanying claims.

Further, as the present inventive concept is susceptible to embodiments of many different forms, it is intended that the present disclosure be considered as an example of the principles of the present inventive concept and not intended to limit the present inventive concept to the specific embodiments shown and described. Any one of the features of the present inventive concept may be used separately or in combination with any other feature. References to the terms "embodiment," "embodiments," and/or the like in the description mean that the feature and/or features being referred to are included in, at least, one aspect of the description. Separate references to the terms "embodiment," "embodiments," and/or the like in the description do not necessarily refer to the same embodiment and are also not mutually exclusive unless so stated and/or except as will be readily apparent to those skilled in the art from the description. For example, a feature, structure, process, step, action, or the like described in one embodiment may also be included in other embodiments, but is not necessarily included. Thus, the present inventive concept may include a variety of combinations and/or integrations of the embodiments described herein. Additionally, all aspects of the present disclosure, as described herein, are not essential for its practice. Likewise, other systems, methods, features, and advantages of the present inventive concept will be, or become, apparent to one with skill in the art upon examination of the figures and the description. It is intended that all such additional systems, methods, features, and advantages be included within this description, be within the scope of the present inventive concept, and be encompassed by the claims.

Lastly, the terms "or" and "and/or," as used herein, are to be interpreted as inclusive or meaning any one or any combination. Therefore, "A, B or C" or "A, B and/or C" mean any of the following: "A," "B," "C"; "A and B"; "A and C"; "B and C"; "A, B and C." An exception to this definition will occur only when a combination of elements, functions, steps or acts are in some way inherently mutually exclusive.

II. General Architecture

Turning to FIG. 1, an apparatus 100 for tissue ablation using radiofrequency (RF) energy is shown. The apparatus 100 includes a housing 102 having a first end 104 extending to a second end 106 and a handle 108 positioned at the second end 106. In an exemplary embodiment, the housing 102 includes a finger rest 110 protruding from a lower surface 112 of the housing 102 to provide a rest or additional grip for a practitioner's finger during use of the apparatus 100, though the housing 102 may not include a finger rest 110 without deviating from the scope of the present inventive concept. The finger rest 110 may be contoured and shaped to receive a finger wrapped around the finger rest 110. The housing 102 may be made of a solid material such as, but not limited to, a plastic, a metal, or the like and may be injection molded or machined. In one example, the housing 102 is a singular, unitary piece, and in another example, the housing 102 is two pieces coupled or adhered together, though the housing 102 may be multiple pieces without deviating from the scope of the present inventive concept. The housing 102 may be hollow to house components of the apparatus 100 such as, but not limited to wiring for one or more light sources 113, wiring to one or more RF probes 118, wiring to an RF source (e.g., an RF generator), wiring to a power source, and/or the power source without deviating from the scope of the present inventive concept.

In the exemplary embodiment, the housing 102 includes a progress indicator 114 positioned on an upper surface 116 of the housing, though the housing 102 may not have a progress indicator 114 without deviating from the scope of the present inventive concept. In the exemplary embodiment, the progress indicator 114 may be positioned space from the practitioner's hand so as to not be obscured by the practitioner's hand, though the progress indicator 114 may be positioned anywhere on the apparatus 100, including at the one or more light sources 113. The progress indicator 114 is coupled to one or more RF probes 118 and/or the RF source and is operable to notify the practitioner of a progress or a completion of an RF treatment administered by the one or more RF probes 116 during use.

In the exemplary embodiment, the progress indicator 114 is a light that pulsates to provide visual feedback, though the progress indicator 114 may be a motor that provides tactile feedback (e.g., vibration) or a display screen that provides another form of visual feedback (e.g., shows a numerical percentage, a progress bar, a progress chart, etc.) without deviating from the scope of the present inventive concept. In another example, the progress indicator 114 is the one or more light sources 113. In yet another example, the progress indicator 114 may be one or more lights that pulsate and/or turn on or off in succession as treatment progresses. In the exemplary embodiment, the progress indicator 114 pulsates more rapidly as the treatment progresses closer to completion and stays lit when completed, though the progress indicator 114 may pulsate more slowly as the treatment progresses closer to completion and turn off when completed, may pulsate in any pattern indicative to the progress and the completion of the treatment, and/or may change colors to indicate progression and/or completion without deviating from the scope of the present inventive concept. Such progress indicator 114 provides visual feedback to the practitioner that is easy visible and quick to view during use. As such, the practitioner can be more aware of ending treatment when the practitioner knows when the treatment is near completion and may more accurately end treatment, thereby reducing over-treatment of the area. Further, the practitioner may be able to communicate to a patient experiencing discomfort that the treatment is near completion, thereby increasing patient comfort.

In the exemplary embodiment, the housing 102 also includes a treatment button 120 positioned on the upper surface 116 that is connected to the RF source, the one or more RF probes 118, the one or more light sources 113, and/or the power source. The treatment button is operable to turn the RF source on or off, thereby turning the RF energy emitted by the one or more RF probes 118 on or off. In another example, the treatment button 120 may additionally turn the apparatus 100 on or off, though the apparatus 100 may be turned on or off by way of connecting the apparatus 100 to the power source (e.g., plugging the apparatus 100 into a power source) without deviating from the scope of the present inventive concept. In another example, the treatment button 120 emits the RF energy when a force is received by the treatment button 120. In other words, the apparatus 100 emits the RF energy as long as the treatment button 120 is pressed by the practitioner, and the apparatus 100 does not emit the RF energy when the treatment button 120 is not pressed by the practitioner. In yet another example, power to the one or more light sources 113 may be toggled by the treatment button 120, or another button not shown, without deviating from the scope of the present inventive concept. In another example, the treatment button 120 is a slider button that may increase the amount of RF energy emitted as the slider button is moved along a slider track.

A tongue depressor 119 extends from the first end 104 of the housing 102 to a tip end 123 and is operable to depress, or hold a tongue down, during treatment. In the exemplary embodiment, the tongue depressor 119 extends in an arc from the first end 104 to the tip end 123, though the tongue depressor 119 may extend in a straight line, a bent line, an angle, or any other shape without deviating from the scope of the present inventive concept. In the exemplary embodiment, the tongue depressor includes a center rib 121, which increases rigidity of the tongue depressor 119, though the tongue depressor 119 may not include a center rib 121 without deviating from the scope of the present inventive concept. The tongue depressor 119 may be made of a solid such as a metal (e.g., steel, stainless steel, aluminum) or a plastic, and may be opaque or transparent. In one example, the tongue depressor 119 may be hollow and may house wiring for the one or more light sources 113 and wiring to the one or more RF probes 118 from the housing 102, though the tongue depressor 119 may be solid without deviating from the scope of the present inventive concept.

Figure 2A:
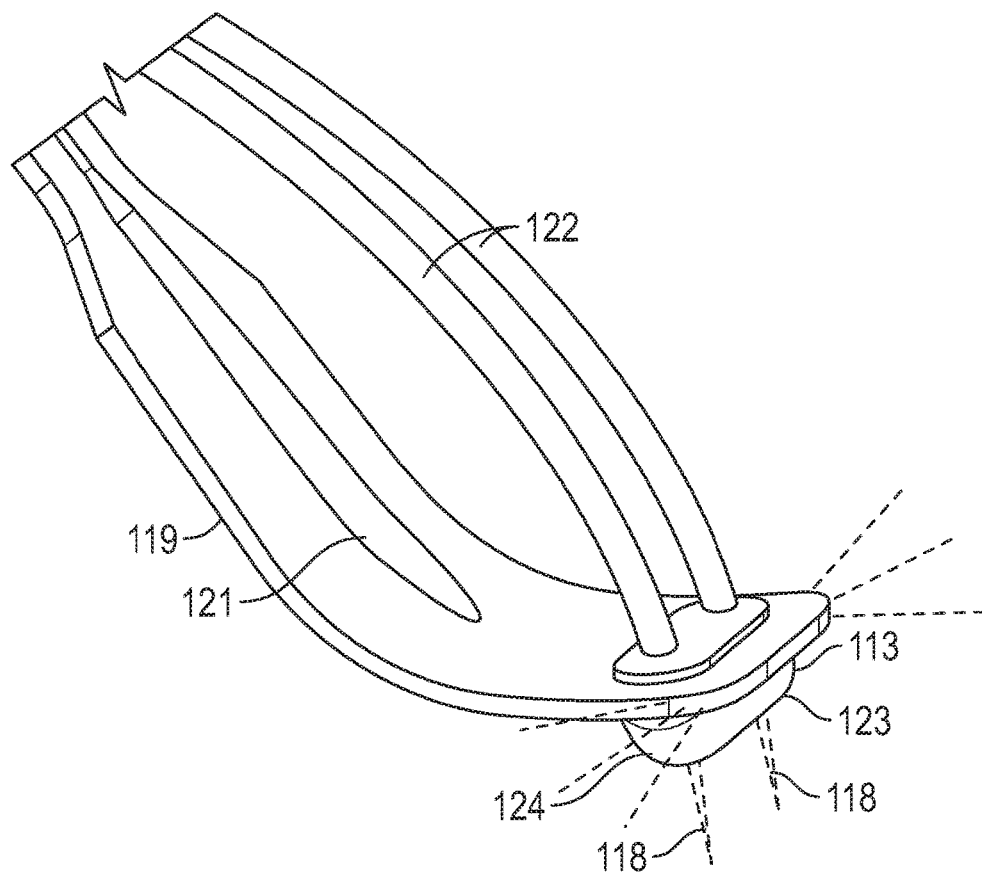
FIG. 2A is a diagram illustrating a detailed, isometric view of a tip end of the apparatus shown in FIG. 1.
Figure 2B:
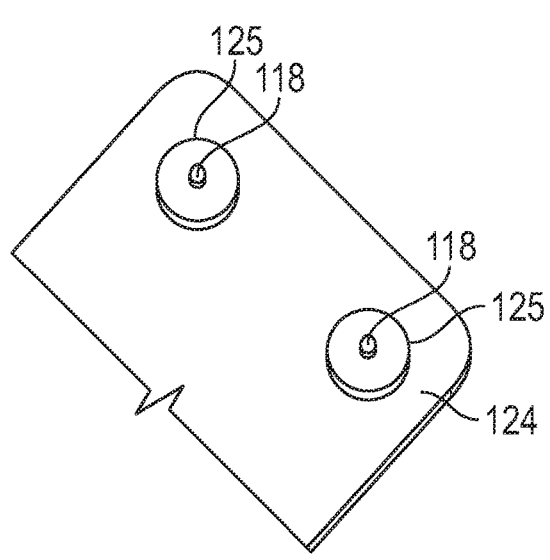
FIG. 2B is a diagram illustrating a detailed, front view of one or more RF probes of the apparatus shown in FIG. 1.

Referring to FIGS. 1, 2A, and 2B, one or more pipes 122 extend from the first end 104 of the housing 102 to a tip end 123. In the exemplary embodiment, the one or more pipes 122 each extend in an arc from the first end 104 to the tip end 122, though the one or more pipes 122 may extend in a straight line, a bent line, an angle, or any other shape, and each pipe 122 may extend in a different shape than each other pipe 122 without deviating from the scope of the present inventive concept. In the exemplary embodiment, the one or more pipes 122 are hollow and receive wiring that extends from the housing 102 to the one or more RF probes 118 positioned at a tip 125 of each of the one or more pipes 122. The one or more RF probes 118 may retract into the tip 125 of each of the one or more pipes 122 and/or a light housing 124. In the exemplary embodiment, the one or more RF probes 118 includes a pair of probes, though the one or more RF probes 118 may include one, two, or more than two RF probes 118 without deviating from the scope of the present inventive concept.

The one or more pipes 122 may also receive wiring that extends from the housing 102 (e.g., the power source) to the one or more light sources 113 positioned at a tip 125 of each of the one or more pipes 122, though the one or more light sources 113 may include an integral power source without deviating from the scope of the present inventive concept. The one or more light sources 113 may also be positioned in the light housing 124, near the first end 104 or the second end 106 of the housing 102, or anywhere on the apparatus 100 without deviating from the scope of the present inventive concept. In one example, the one or more light sources 113 are LEDs. The one or more pipes 122 may be made of a solid such as a metal (e.g., steel, stainless steel, aluminum) or a plastic. In the exemplary embodiment, the one or more pipes 122 are opaque. In another embodiment, the one or more pipes 122 may be transparent and may include an elongate light source extending through one or more pipes 122 or multiple light sources positioned in the one or more pipes 122 to illuminate each of the one or more pipes 122 without deviating from the scope of the present inventive concept. Illumination provided by the one or more light sources 113 may help the practitioner to see and identify a target treatment area. Further, improved illumination at the target treatment area may help the practitioner maintain positioning of the apparatus 100 at the treatment area, thereby improving delivery of the treatment.

Figure 2C:
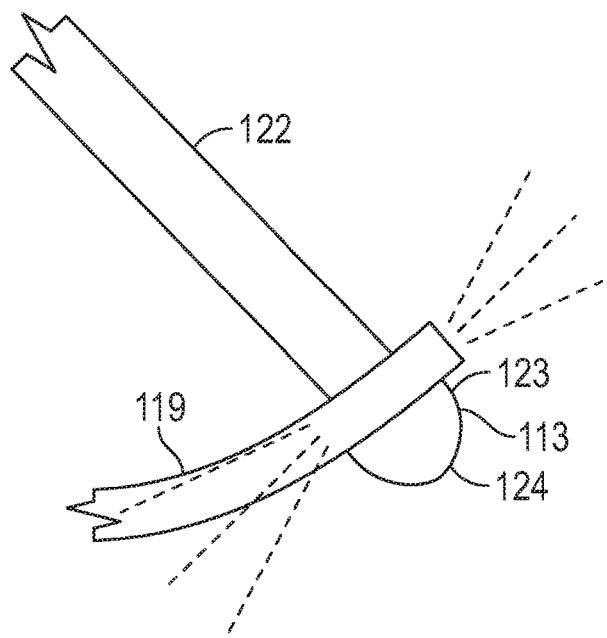
FIG. 2C is a diagram illustrating a side view of the tip end of the apparatus shown in FIG. 1 with the one or more RF probes retracted, and illustrating a first embodiment of a light housing operable to house one or more light sources.
Figure 3C:
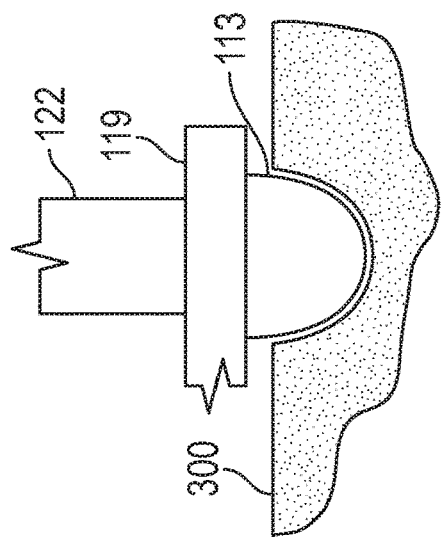
FIG. 3C is a diagram illustrating a side, cross-sectional view of the first embodiment of the one or more light sources, shown in FIG. 2C, emitting a light path in a soft tissue.
Figure 3B:
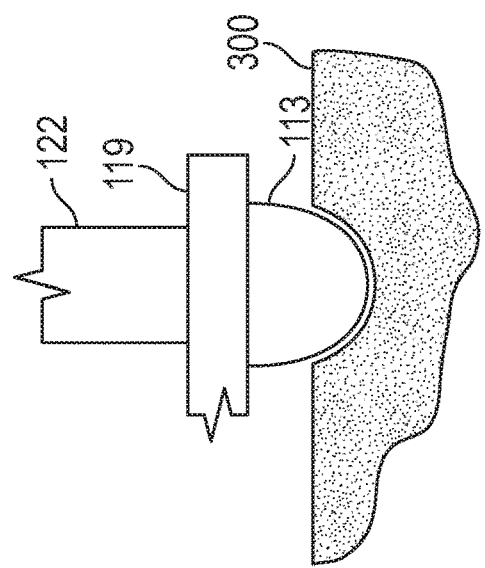
FIG. 3B is a diagram illustrating a side, cross-sectional view of the first embodiment of the one or more light sources, shown in FIG. 2C, emitting a light path in a firm-soft tissue.
Figure 3A:
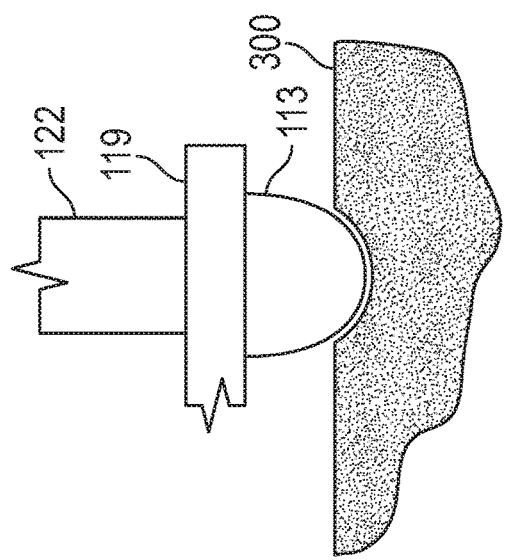
FIG. 3A is a diagram illustrating a side, cross-sectional view of the first embodiment of the one or more light sources, shown in FIG. 2C, emitting a light path in a firm tissue.
Figure 4A:
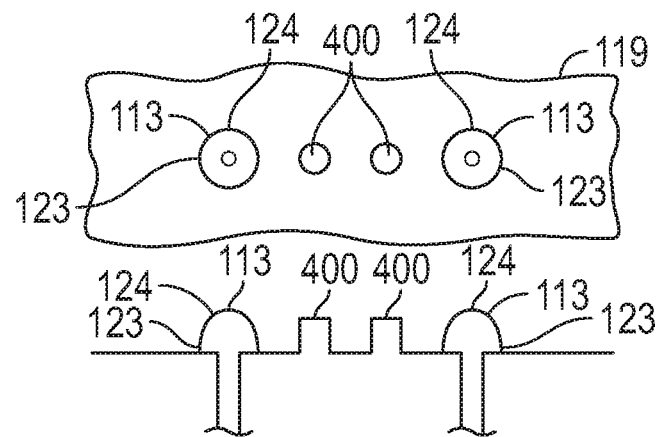
FIG. 4A is a diagram illustrating a front and a side view of the tip end of the apparatus shown in FIG. 1 with the one or more probes retracted, and illustrating a second embodiment of a light housing operable to house one or more light sources.

Turning to FIG. 2C, a side view of the tip end 123 of the apparatus 100 shown in FIG. 1 with the one or more RF probes 118 retracted and the one or more light sources 113 is shown in the light housing 124 emitting a light path. In a first exemplary embodiment, the light housing 124 is a single-piece housing in the shape of an elongated dome, as shown in FIG. 2A. In another example, the light housing 124 is two dome-shaped pieces, as shown in FIG. 2B, and 4A, though the light housing 124 may be any shape or may be one, two, or more than two pieces without deviating from the scope of the present inventive concept. In the exemplary embodiment, the light housing 124 is transparent, though the light housing 124 may be translucent, or any grade of transparency without deviating from the scope of the present inventive concept. The light housing 124 is further shaped such that when the light housing 124 is pressed against tissue of the patient, a portion or none of a light path emitted by the one or more light sources 113 may be visible during use. For example, in FIGS. 3A-3C, the light housing 124 is shown in a cross-sectional view of a tissue 300 that is firm, tissue 300 that is firm-soft, and tissue 300 that is soft. The tissue 300 that is firm will yield less than tissue that is firm-soft or soft and as such, the light housing 124 will be more covered and less of the light path emitted by the one or more light sources 113 will be visible in softer tissue. For example, more of the light housing 124 is covered by the tissue 300 that is firm-soft shown in FIG. 3B than the tissue 300 that is firm shown in FIG. 3A, and thus less of the light path is visible in the firm-soft tissue 300 than the firm tissue 300. In another example, the light housing 124 is more covered by the tissue 300 that is soft shown in FIG. 3C than the tissue 300 that is firm-soft shown in FIG. 3B, and thus less of the light path is visible in the soft tissue 300 than the firm-soft tissue 300. An amount of the light path that is returned (i.e., is visible) indicates a thickness of the tissue 300 and as more of the light housing 124 is covered, less of the light path is returned. As such, a decrease in the light path returned indicates a softer tissue 300 (e.g., more of the light housing 124 is covered) and an increase in the light path that is returned indicates a firmer tissue 300 (e.g., less of the light housing 124 is covered).

Figure 4B:
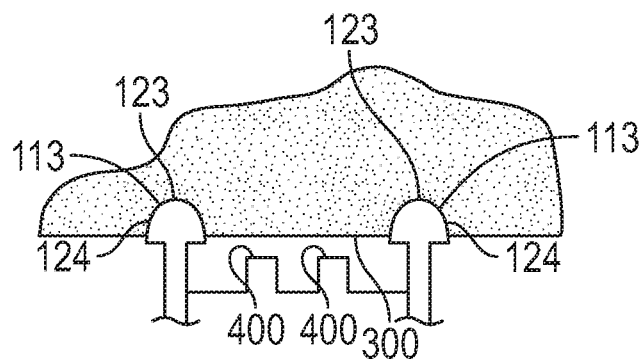
FIG. 4B is a diagram illustrating a side, cross-sectional view of the second embodiment of the one or more light sources, shown in FIG. 4A, emitting the light path in a soft tissue.
Figure 4C:
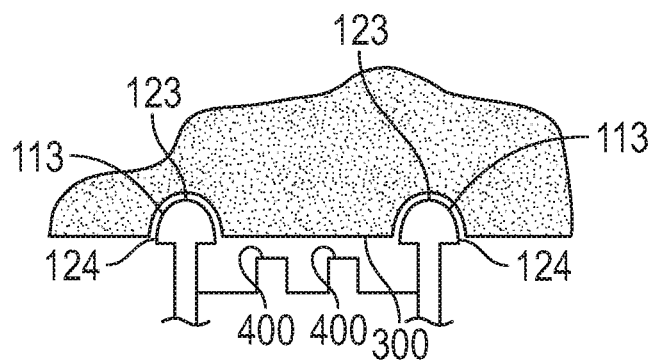
FIG. 4C is a diagram illustrating a side, cross-sectional view of the second embodiment of the one or more light sources, shown in FIG. 4A, emitting the light path in a firm tissue.

The light path may be viewed directly by the practitioner to determine the thickness of the tissue 300, or one or more sensors 400, as shown in FIGS. 4A-4C, may be operable to detect the amount of the light path that is returned. In the exemplary embodiment the one or more sensors 400 are a pair of photodiodes positioned in between two light housings 124 and on a portion of the tongue depressor 119 that couples to the one or more light pipes 122, though the one or more sensors 400 may be any sensor such as a force sensor, may be positioned anywhere on the apparatus 100, and may include one, two, or more than two sensors without deviating from the scope of the present inventive concept. The one or more sensors 400 may be operable to indicate to the practitioner, the thickness of the tissue 300, based on the amount of the detected amount of the light path that is returned. As previously described, and shown in FIGS. 4B-4C, the light housing 124 is covered less or a gap between the tissue 300 and the light housing 124 may be formed in the firm tissue 300, shown in FIG. 4C, than the soft tissue 300, shown in FIG. 4B, thereby, more of the light path is returned and detected by the one or more sensors 400 in the firm tissue 300 than the soft tissue 300. In the exemplary embodiment, the amount of the light path detected by the one or more sensors 400 is be communicated to the practitioner by the progress indicator 114, though the amount of light path detected can be communicated by a sound emitted, a vibration, or a screen without deviating from the scope of the present inventive concept. In another example, a blinking LED may indicate the thickness of the tissue 300 wherein the LED may be off if the light housings 124 are not covered by any tissue 300, the LED may blink slowly if the light housings 124 are partially covered, and the LED stays illuminated if the light housings 124 are fully covered during use. Identifying the tissue thickness may aid the practitioner in determining treated tissue 300 and tissue 300 that needs to be treated. Such identification may improve the accuracy of the practitioner in locating an area of tissue 300 to be treated.

Figure 5:
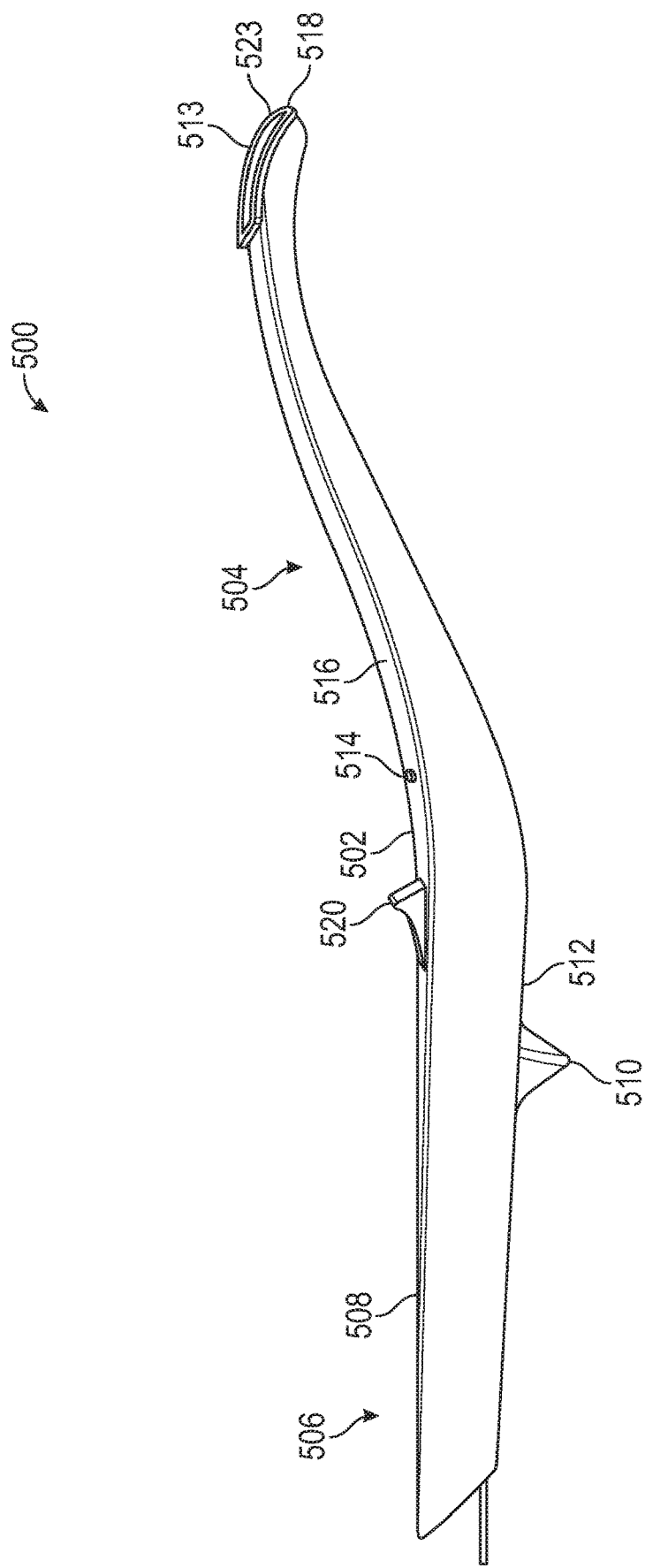
FIG. 5 is a diagram illustrating an isometric view of another embodiment of an apparatus for tissue ablation using RF energy.

Turning to FIG. 5, another apparatus 500 for tissue ablation using RF energy is illustrated. The apparatus 500 includes a housing 502 having a first end 504 extending to a second end 506 and a handle 508 positioned at the second end 506. In an exemplary embodiment, the housing 502 includes a finger rest 510 protruding from a lower surface 512 of the housing 502 to provide a rest or additional grip for a practitioner's finger during use of the apparatus 500, though the housing 502 may not include a finger rest 510 without deviating from the scope of the present inventive concept. The finger rest 510 may be contoured and shaped to receive a finger wrapped around the finger rest 510. The housing 502 may be made of a solid material such as, but not limited to, a plastic, a metal, or the like and may be injection molded or machine. In one example, the housing 502 is a singular, unitary piece, and in another example, the housing 502 is two pieces coupled or adhered together, though the housing 502 may be multiple pieces without deviating from the scope of the present inventive concept. The housing 502 may be hollow to house components of the apparatus 500 such as, but not limited to wiring for one or more light sources 513, wiring to the RF surface 518, wiring to an RF source (e.g., an RF generator), wiring to a power source, and/or the power source without deviating from the scope of the present inventive concept.

In the exemplary embodiment, the housing 502 includes a progress indicator 514 positioned on an upper surface 516 of the housing, though the housing 502 may not have a progress indicator 514 without deviating from the scope of the present inventive concept. In the exemplary embodiment, the progress indicator 514 may be positioned space from the practitioner's hand so as to not be obscured by the practitioner's hand, though the progress indicator 514 may be positioned anywhere on the apparatus 500, including at the one or more light sources 513. The progress indicator 514 is coupled to the RF surface 518 and/or the RF source and is operable to notify the practitioner of a progress or a completion of an RF treatment administered by the one or more RF probes 516.

In the exemplary embodiment, the progress indicator 514 is a light that pulsates to provide visual feedback, though the progress indicator 514 may be a motor that provides tactile feedback (e.g., vibration) or a display screen that provides another form of visual feedback (e.g., shows a numerical percentage, a progress bar, a progress chart, etc.) without deviating from the scope of the present inventive concept. In another example, the progress indicator 514 is the one or more light sources 513. In yet another example, the progress indicator 514 may be one or more lights that pulsate and/or turn on or off in succession as treatment progresses. In the exemplary embodiment, the progress indicator 514 pulsates more rapidly as the treatment progresses closer to completion and stays lit when completed, though the progress indicator 514 may pulsate more slowly as the treatment progresses closer to completion and turn off when completed, may pulsate in any pattern indicative to the progress and the completion of the treatment, and/or may change colors to indicate progression and/or completion without deviating from the scope of the present inventive concept. Such progress indicator 514 provides visual feedback to the practitioner that is easy visible and quick to view. As such, the practitioner can be more aware of ending treatment when the practitioner knows when the treatment is near completion and may more accurately end treatment, thereby reducing over-treatment of the area. Further, the practitioner may be able to communicate to a patient experiencing discomfort that the treatment is near completion, thereby increasing patient comfort.

In the exemplary embodiment, the housing 502 also includes a treatment button 520 positioned on the upper surface 516 that is connected to the RF source, the RF surface 518, the one or more light sources 513, and/or the power source. The treatment button is operable to turn the RF source on or off, thereby turning the RF energy emitted by the RF surface 518 on or off. In another example, the treatment button 520 may additionally turn the apparatus 500 on or off, though the apparatus 500 may be turned on or off by way of connecting the apparatus 500 to the power source (e.g., plugging the apparatus 500 into a power source) without deviating from the scope of the present inventive concept. In another example, the treatment button 520 emits the RF energy when a force is received by the treatment button 520. In other words, the apparatus 500 emits the RF energy as long as the treatment button 520 is pressed by the practitioner, and the apparatus 500 does not emit the RF energy when the treatment button 520 is not pressed by the practitioner. In yet another example, power to the one or more light sources 513 may be toggled by the treatment button 520, or another button not shown, without deviating from the scope of the present inventive concept. In another example, the treatment button 520 is a slider button that may increase the amount of RF energy emitted as the slider button is moved along a slider track.

The apparatus 500 includes a tip end 523 having the RF surface 518 and the one or more light sources 513. In the exemplary embodiment the tip end 523 is curved to fit against a soft palate tissue of the patient. During use, the one or more light sources 513 are operable to light a treatment area of the patient. The one or more light sources 513 may include an integral power source without deviating from the scope of the present inventive concept. The one or more light sources 513 may also be positioned in the light housing 524, near the first end 504 or the second end 506 of the housing 502, or anywhere on the apparatus 500 without deviating from the scope of the present inventive concept. In one example, the one or more light sources 513 are LEDs.

During use, the apparatus 100, 500 is inserted into a patient's mouth by a practitioner and guided to tissue 300 to be treated by the practitioner. The patient's mouth is illuminated by the one or more light sources 113, 513 such that the practitioner may accurately identify the tissue 300 to be treated. The one or more light sources 113, 513 may emit one or more light paths into the tissue 300. A portion of the one or more light paths may be received by one or more sensors 400 housed in the tip 125 of the one or more light pipes 122. The practitioner may be notified by the progress indicator 114, 514 of the thickness of the tissue 300 based on an amount of the one or more light paths received.

The apparatus 100, 500 provides multiple benefits to the practitioner. The practitioner may be able to more accurately locate and identify tissue 300 to be treated, by the one or more light sources 113, 513 and notification or indication of a thickness of the tissue 300. The practitioner may also be able to provide up-to-date progress to the patient during treatment, by easily viewing the progress indicator 114 within the practitioner's line of sight during use. As such, the apparatus 100, 500 may increase accuracy of the location of treatment and administration of the treatment by the practitioner, thereby increasing effectiveness of the treatment.

One of skill in the art will recognize that the described examples are not limited to any particular size. Further, one of skill in the art will recognize that the components of the apparatus 100 are not limited to any type of material. In a preferred example, the apparatus 100 is formed of one or more plastics, but may be formed of a variety of different materials including metal or the like or rubber or the like, or a combination thereof. One skilled in the art will recognize that different diameters, types, and thicknesses of preferred materials can be utilized when taking into consideration design and stability considerations. A number of manufacturing techniques may be used such as the molding, machining, and/or casting one or more components of the foot clip. An example process of manufacturing the apparatus 100 includes use of an injection molding process or other like manufacturing means.

It will be appreciated by those skilled in the art that changes could be made to the embodiments described above without departing from the broad inventive concept thereof. It is understood, therefore, that the present invention disclosed herein is not limited to the particular embodiments disclosed, and is intended to cover modifications within the spirit and scope of the present invention.

The invention claimed is:

1. An apparatus for delivering radio-frequency (RF) energy, the apparatus comprising:
   a housing extending from a first end to a second end and having an upper surface;
   one or more pipes extending from the first end, the one or more pipes terminating at a tip, the tip having a light source operable to provide light;
   a probe extending from some of the one or more pipes, the probe operable to deliver RF energy and to extend from or retract into the tip;
   a tongue depressor extending from the first end of the housing and extending separately from and below the one or more pipes, the tongue depressor immovably secured to the one or more pipes at the tip;
   a light sensor disposed at the tip operable to receive a portion of a light path generated by the light source; and
   a progress indicator disposed on the upper surface to provide an auditory, visual, or tactile indication of an amount of progress of an event based at least partly on the portion of the light path received by the light sensor.

2. The apparatus of claim 1, wherein, the probe extends from each of the one or more pipes.

3. The apparatus of claim 1, further comprising a handle positioned at the second end of the housing.

4. The apparatus of claim 1,
   wherein, the portion of the light path received indicates a thickness of a tissue.

5. The apparatus of claim 1,
   wherein,
   the tongue depressor includes a rigid center rib.

6. The apparatus of claim 1,
   wherein,
   the one or more pipes includes a hollow core to receive a wire for each light source, the wire connecting the light source to a power source.

7. An apparatus for determining a thickness of a tissue, the apparatus comprising:
   a housing extending from a first end to a second end and having an upper surface;
   one or more pipes extending from the first end, the one or more pipes terminating at a tip;
   a light source protruding from the tip of the one or more pipes, the light source operable to send one or more light paths;
   a tongue depressor extending from the first end of the housing and extending separately from and below the one or more pipes, the tongue depressor immovably secured to the one or more pipes at the tip;
   a sensor operable to receive a portion of the light path, the sensor housed in a light housing, the light housing positioned at the tip of the one or more pipes; and a progress indicator disposed on the upper surface to provide an auditory, visual, or tactile indication of an amount of progress of an event based at least partly on the portion of the light path received by the sensor, wherein,
the portion of the light path received indicates a thickness of a tissue.

8. The apparatus of claim 7, further comprising:
a handle positioned at the second end of the housing.

9. The apparatus of claim 7,
wherein,
the event is the portion of the light path received.

10. The apparatus of claim 7, further comprising:
a probe extending from some of the one or more pipes, the probe operable to deliver radio-frequency (RF) energy and to extend from or retract into the tip.

11. The apparatus of claim 10,
wherein,
the event is delivery of the RF energy.

12. The apparatus of claim 7, further comprising:
another sensor operable to detect a force received from a user of the apparatus.

13. A method for determining a thickness of a tissue, the method comprising:
transmitting, by one or more light sources, one or more light paths into a tissue of a patient, each of the one or more light sources extending from a tip of one or more pipes, the one or more pipes extending from a housing;
depressing a tongue with a tongue depressor that extends from the housing separately from and below the one or more pipes and immovably secures to the one or more pipes at the tip;
receiving, by one or more sensors, a portion of the one or more light paths, the one or more sensors housed in the tip of the one or more pipes; and
notifying, by a progress indicator disposed on an upper surface of the housing, a user of the thickness of the tissue by providing an auditory, visual, or tactile indication of an amount of progress of an event based on the portion of the one or more light paths received.

14. The method of claim 13, further comprising:
delivering, via a probe, radio-frequency energy to the tissue, the probe extending from some of the one or more pipes.

15. The apparatus of claim 1,
wherein,
the progress indicator includes a light that pulsates at a rate indicating the amount of progress.

16. The apparatus of claim 1,
wherein,
the progress indicator includes a display representing the amount of progress as a numerical percentage or a progress bar.

17. The apparatus of claim 1,
wherein,
the event is an incomplete event and the progress indicator indicates the amount of progress as a percentage of completion for the incomplete event.

18. The apparatus of claim 1,
wherein,
the one or more pipes defines an arc and the tongue depressor defines a straight or bent line that is different than the arc.

19. The apparatus of claim 1,
wherein,
the tongue depressor extends from the first end of the housing with space between the tongue depressor and the one or more pipes at the first end of the housing.

20. The method of claim 13,
wherein,
the progress indicator is disposed on the upper surface of the housing between:
a first end of the housing from which the one or more pipes extend; and
a second end of the housing that includes a handle of the housing.

* * * * *